Aug. 8, 1972 W. H. JESSEL, JR., ET AL Plant Pat. 3,250
CHRYSANTHEMUM PLANT
Filed Dec. 21, 1970
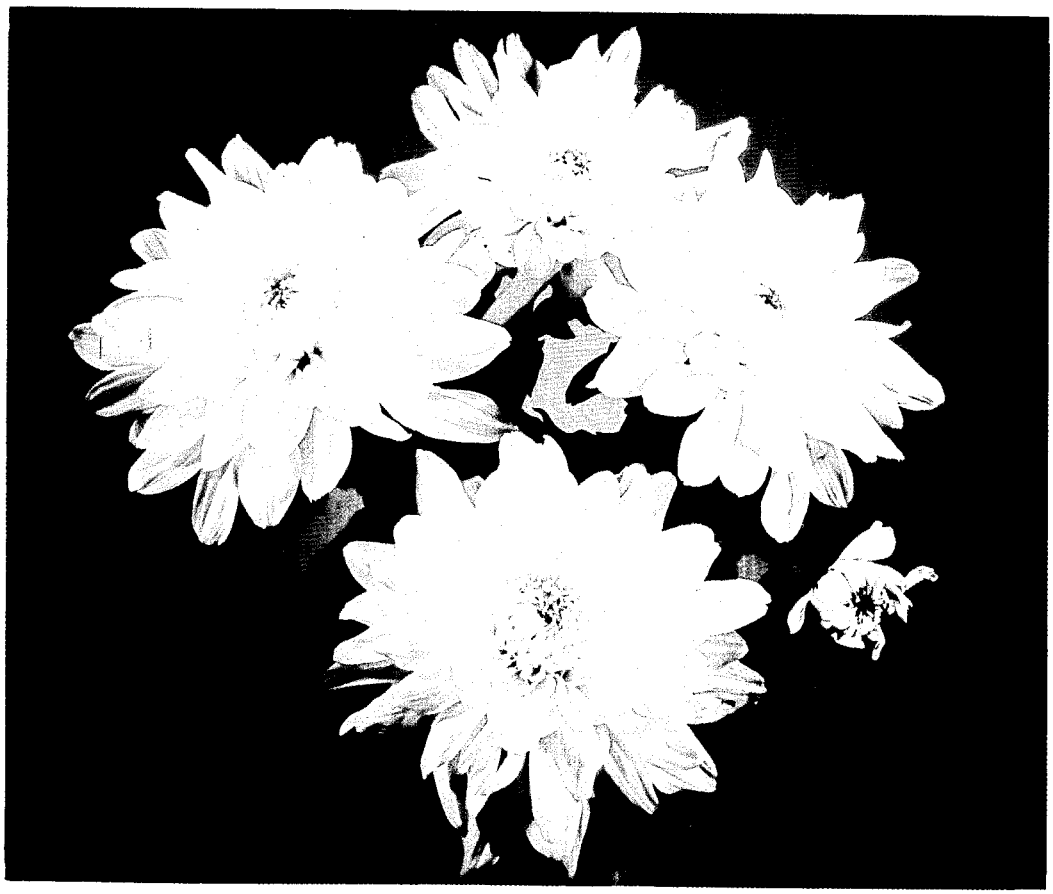
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,250
Patented Aug. 8, 1972

3,250

CHRYSANTHEMUM PLANT

Walter H. Jessel, Jr., Doylestown, and William E. Duffett, Akron, Ohio, assignors to Yoder Brothers, Inc., Barberton, Ohio

Filed Dec. 21, 1970, Ser. No. 100,556
Int. Cl. A01h *5/00*
U.S. Cl. Plt.—78 1 Claim

The present invention comprises a new and distinct cultivar of chrysanthemum plant which is a sport of the cultivar Mountain Snow. The latter is a commercial cultivar of Yoder Brothers, Inc., Barberton, Ohio, and forms the subject matter of an application for U.S. Letters Patent, filed Oct. 14, 1970, Ser. No. 80,823.

The new cultivar is similar in many respects to Mountain Snow, having the same characteristics of:

(1) Decorative flower form.
(2) Identical flowering period and ten week response.
(3) Foliage shape and color.

The new cultivar is distinguished from Mountain Snow by the following characteristics:

(1) Yellow flower color.
(2) 2"–3" shorter habit.
(3) 1" more plant spread.
(4) Flowers approximately ¼" smaller at the two-thirds open stage to 1¼" smaller when fully mature and expanded.
(5) A petal about 5/16" narrower in width.
(6) Leaves ¾" shorter in length.
(7) 2–3 days later response.

The new cultivar was selected from a flowering block of the parent cultivar at Barberton, Ohio, and has been asexually reproduced by cuttings at Barberton, Ohio, and has been found to retain its distinctive characteristics through successive propagations.

The new cultivar when grown in the vicinity of Barberton, Ohio, has a response period of approximately ten weeks, and the following detailed description is based on observations made of the new cultivar in a greenhouse in Barberton, Ohio. The response time, blooming period, total vigor, and color may vary significantly with varying environmental conditions such as temperature, day length, and light intensity. Suggested flowering in the northern and northwestern United States is March through November. The cultivar tends to develop a longitudinal petal roll in December, January and February during low light periods, and also lacks good flower and plant qualities under very low light conditions. Suggested flowering in the southern United States if from January through December, and in Florida, December through April.

The accompanying drawing shows the unique characteristics of the new cultivar, the color being as nearly true as possible with color illustrations of this type.

In the following description, color references are to the Munsell Color Book, 1963 edition, and comparisons have been made where significant differences in characteristics exist with the parent cultivar Mountain Snow.

Botanical classification: *Chrysanthemum morifolium*

| | Mountain Sun | Mountain Snow |
|---|---|---|
| Bloom: | | |
| Size | 4¾" | 5". |
| Fully expanded | 5¼" | 6½". |
| Borne | Terminal on disbudded branches. | |
| Stems | Strong | |
| Form | Decorative | |
| Permanence | 10–12 days | |
| Color: | | |
| Center of flower. | Dark yellow, 7.5Y8.5/12. | Light green, 2.5GY9/6 to ivory white, 7.5Y9/2. |
| Base of petals | do | Light green, 2.5GY9/6. |
| Inside of petals. | Yellow, 7.5Y8.5/8 to light yellow, 7.5Y9/6. | White, N9.5/. |
| Reverse of petals. | Light yellow, 7.5Y9/6 | Do. |
| Tonality from a distance. | Yellow | White. |
| Discoloration | Light yellow, 7.5Y9/6 | White, N9.5/. |
| Petals: | | |
| Texture | Smooth | Smooth. |
| Appearance and form. | Open at base broadening to ¾" wide. Broad shallow keel. | Open at base broadening quickly to 1 1/16" wide. Very broad shallow keel. |
| Arrangement | Composite, whorled on a single receptacle. | |
| Persistence | Resist shatter | |
| Fragrance | Typical chrysanthemum | |
| Reproductive organs: | | |
| Stamen, anthers | None to 30–40 | |
| Pollen | None to very scant | |
| Arrangement | Clustered in center of flower, if present. | |
| Styles | Present both ray and disc florets | |
| Length | Short | |
| Ovaries | At the base of petal attached to receptacle | |
| Plant: | | |
| Form | Herbaceous | |
| Growth | Semi-upright | |
| Height | Approximately 13" when given 10 week Tall treatment as defined in the timetables of Yoder Brothers, Inc. | Approximately 15½" when given 10 week Medium treatment as defined in the timetables of Yoder Brothers, Inc. |
| Spread | Approximately 9½" when given 10 week Medium treatment as defined in the timetables of Yoder Brothers, Inc. | Approximately 8½" when given 10 week Medium treatment as defined in the timetables of Yoder Brothers, Inc. |
| Foliage: | | |
| Top side | Green, 7.5GY3/4 | |
| Size | 4¼" long, 2¾" wide | 5" long, 3" wide. |
| Quantity | Numerous | |
| Shape | Spatulate lobed | |
| Texture | Smooth | |
| Ribs and veins | Slight prominence | |
| Edge | Slightly indented | |
| Serration | Very slight | |
| Underside | Light green, 7.5GY5/4 | |
| Stipules | Very prominent | |

We claim:

1. A new and distinct cultivar of chrysanthemum characterized particularly as to uniqueness when compared to the parent cultivar Mountain Snow by its light yellow color, 2"–3" shorter habit, 2–3 days later response, 1" more plant spread, ¼"–1¼" smaller flowers, a flower petal 5/16" narrower, and leaves ¾" shorter.

No references cited.

ROBERT E. BAGWILL, Primary Examiner